United States Patent
Rao et al.

(10) Patent No.: US 8,247,434 B2
(45) Date of Patent: Aug. 21, 2012

(54) FEXOFENADINE POLYMORPHS AND PROCESSES OF PREPARING THE SAME

(75) Inventors: Dharmaraj Ramachandra Rao, Maharashtra (IN); Rajendra Narayanrao Kankan, Maharashtra (IN); Manish Gopaldas Gangrade, Maharashtra (IN); Dilip Ramdas Birari, Maharashtra (IN)

(73) Assignee: Cipla Limited, Mumbai (IN)

( * ) Notice: Subject to any disclaimer, the term of this patent is extended or adjusted under 35 U.S.C. 154(b) by 741 days.

(21) Appl. No.: 12/274,077

(22) Filed: Nov. 19, 2008

(65) Prior Publication Data
US 2009/0221830 A1    Sep. 3, 2009

Related U.S. Application Data

(62) Division of application No. 10/569,611, filed as application No. PCT/GB2004/003624 on Aug. 25, 2004, now Pat. No. 7,470,789.

(30) Foreign Application Priority Data

Aug. 26, 2003    (GB) .................................. 0319935.3

(51) Int. Cl.
*A61K 31/445*    (2006.01)
*C07D 211/22*    (2006.01)
(52) U.S. Cl. .................. 514/327; 546/239; 546/240
(58) Field of Classification Search .................. 514/327; 546/239, 240
See application file for complete search history.

(56) References Cited

U.S. PATENT DOCUMENTS

| 4,254,129 | A | 3/1981 | Carr et al. |
|---|---|---|---|
| 5,654,433 | A | 8/1997 | King et al. |
| 7,135,571 | B2 | 11/2006 | Henton et al. |
| 7,470,789 | B2 | 12/2008 | Rao et al. |
| 2002/0177608 | A1 | 11/2002 | Dolitzky et al. |
| 2005/0165056 | A1 | 7/2005 | Kirsch |

FOREIGN PATENT DOCUMENTS

| EP | 1178041 A1 | 2/2002 |
|---|---|---|
| EP | 0766668 B1 | 7/2002 |
| WO | 9321156 A1 | 10/1993 |
| WO | 9500482 A1 | 1/1995 |
| WO | 9531437 A1 | 11/1995 |
| WO | 0194313 A2 | 12/2001 |
| WO | 0194313 A3 | 12/2001 |
| WO | 02066429 A1 | 8/2002 |
| WO | 02080857 A2 | 10/2002 |
| WO | 02102777 A2 | 12/2002 |

(Continued)

OTHER PUBLICATIONS

Braga et al. "Making crystals . . ." J. Roy. Soc, Chem. Chem. Comm. p. 3635-3645 (2005).*

(Continued)

*Primary Examiner* — Celia Chang
(74) *Attorney, Agent, or Firm* — Conley Rose, P.C.; Rodney B. Carroll

(57) ABSTRACT

Anhydrous crystalline fexofenadine hydrochloride Form C, crystalline fexofenadine acetate monohydrate Form D, crystalline fexofenadine acetate dihydrate Form E and crystalline fexofenadine free base monohydrate Form F, processes of preparing the same, pharmaceutical compositions thereof, therapeutic uses thereof and methods of treatment therewith.

16 Claims, 9 Drawing Sheets

FOREIGN PATENT DOCUMENTS

| WO | 03011295 | A1 | 2/2003 |
| WO | 03039482 | A2 | 5/2003 |
| WO | 03104197 | A1 | 12/2003 |
| WO | 2005019175 | A1 | 3/2005 |

OTHER PUBLICATIONS

Kirk=Othmer "crystallization" Encyclopedia of chem. tech. v.8, p. 95-147 (2002).*

Polymorphism "Background information . . ." ACPS meeting p. 1-5 (2002).*

Seddon "Pseudopolymorph . . ." Crystal Growth & design 4(6) 1087 (2004) (two page form internet).*

Foreign communication from a priority application—International Preliminary Report on Patentability, PCT/GB2004/003624, Feb. 27, 2006, 9 pages.

Foreign communication from a priority application—International Search Report and Written Opinion, PCT/GB2004/003624, Jan. 27, 2005, 16 pages.

Kawai, Stephen H., "A facile synthesis of an oxidation product of terfenadine," XP-002064406, 1994, pp. 2620-2622, vol. 59, No. 9, J. Org. Chem.

* cited by examiner

FEXOFENADINE POLYMORPHS AND PROCESSES OF PREPARING THE SAME

CROSS-REFERENCE TO RELATED APPLICATIONS

This is a Divisional Application of U.S. patent application Ser. No. 10/569,611, filed Oct. 18, 2006 and published as US 2007/0191428 A1, and entitled "Fexofendine Polymorphs and Processes of Preparing the Same," which was a filing under 35 U.S.C. 371 of International Application No. PCT/GB2004/003624 filed Aug. 25, 2004, entitled "Fexofenadine Polymorphs and Processes of Preparing the Same," claiming priority of Great Britain Patent Application 0319935.3 filed Aug. 26, 2003, which applications are incorporated by reference herein in their entirety.

FIELD OF THE INVENTION

The present invention is concerned with fexofenadine polymorphs, processes of preparing the same and the use thereof in pharmaceutical formulations and methods of antihistaminic treatment.

4-[4-[4-(hydroxydiphenylmethyl)-1-piperidinyl]-1-hydroxybutyl]-α,α-dimethylbenzeneacetic acid of formula (I), fexofenadine, is an $H_1$ receptor antagonist and a useful antihistaminic drug

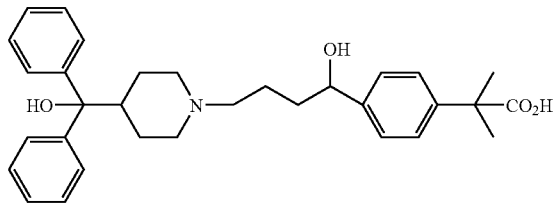

(I)

BACKGROUND OF THE INVENTION

Various pharmaceutically acceptable salts of fexofenadine have been disclosed, for example EP 1178041A, page 5, paragraph 0010. EP 1178041A further describes the preparation of anhydrous fexofenadine hydrochloride (Forms I and III) and hydrated forms (Forms II and Form IV). The process described in EP 1178041A involves making the anhydrous Forms I and III from the hydrated Forms II and IV, for example by azeotropic distillation thus heating in acidic conditions for extended periods. Extended heating in this way can cause following impurities I and II to increase beyond acceptable levels

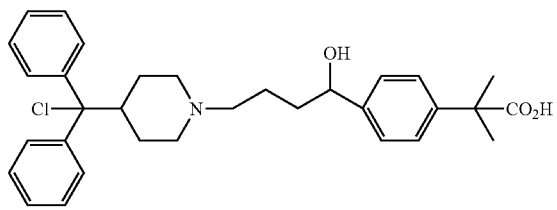

Impurity I

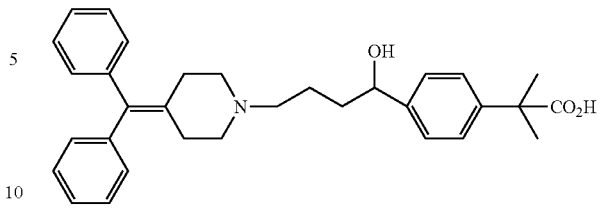

Impurity II

EP 1178041A also describes a water-limiting crystallization that involves crystallization of the hydrate, but this involves using large volumes of solvent so as to limit the water content of the solution to acceptable levels.

WO 01/94313 describes Form A of fexofenadine hydrochloride. The process for its preparation involves the use of water, which means Form A is prepared as a hydrated form, which is not suitable for pharmaceutical formulation.

U.S. Pat. No. 4,254,129 is the basic fexofenadine patent and describes fexofenadine HCl being isolated from aqueous hydrochloric acid, which will lead to the formation of a hydrated form, which as indicated above is not suitable for pharmaceutical formulation.

WO 93/21156 also relates to fexofenadine hydrochloride and Example 1 describes dissolving fexofenadine base in methylene dichloride and acidifying with HCl gas to pH 3. The reaction mass is then concentrated to residue, ether is added and the mixture is stirred to obtain solid, which is filtered to give fexofenadine hydrochloride. This process leads to the formation of amorphous fexofenadine hydrochloride, which has a tendency to pick up moisture and form lumps on storage, and as such is difficult to handle during formulation of tablets and capsules. Furthermore, the use of ether as described in the preparation thereof is not advisable on a commercial scale and hence the process described therein is unsuitable for industrial application.

Apart from the hydrochloride salt, in anhydrous and hydrated forms as discussed above, however, no other salt of fexofenadine has been exemplified in the prior art. Conversion of hydrated salts to their anhydrous forms by water minimizing crystallization is also claimed in EP 766668B, but the disclosure is limited to the inter-conversion of corresponding salts. The conversion of one salt, hydrated or otherwise, to a different anhydrous salt form is not reported or suggested.

SUMMARY OF THE INVENTION

The present invention now provides novel polymorphs of fexofenadine, whereby a first salt of fexofenadine in hydrated form can be converted directly to a different salt of fexofenadine in anhydrous form. More particularly, we have now found that fexofenadine acetate, and its hydrated forms, can be converted to a novel polymorph of anhydrous fexofenadine hydrochloride, which is distinguished from the fexofenadine hydrochloride polymorphs described in the prior art in respect of its melting point range, X-ray diffraction pattern and infra red absorption spectrum. Furthermore, advantages can be shown in respect of anhydrous fexofenadine hydrochloride according to the present invention compared to the prior art, for example the avoidance of associated impurities (such as impurities I and II described above) and also the free flowing nature thereof, which renders anhydrous fexofenadine hydrochloride according to the present invention particularly suitable for formulation use.

The present invention also provides fexofenadine free base monohydrate which can also be converted to the above novel polymorph of anhydrous fexofenadine hydrochloride.

DETAILED DESCRIPTION OF THE INVENTION

More particularly, there is provided by the present invention anhydrous crystalline fexofenadine hydrochloride Form C.

The present invention also provides anhydrous crystalline fexofenadine hydrochloride Form C having an X-ray diffraction pattern, or substantially the same X-ray diffraction pattern, as shown in FIG. 1. More particularly, anhydrous crystalline fexofenadine hydrochloride Form C according to the present invention can be characterised as having an X-ray diffraction pattern with characteristic peaks (2θ): 8.9712°, 14.8293°, 16.0514°, 17.0775°, 18.3418°, 19.3099°, 19.7703°, 21.1340°, 21.5207°, 23.0743° and 23.8286°.

Further characterising data for anhydrous crystalline fexofenadine hydrochloride Form C according to the present invention as obtained by X-ray diffraction is shown in following table 1.

TABLE 1

| Peak No. | 2θ (deg) | d (A) | I/II |
|---|---|---|---|
| 1 | 6.0640 | 14.56317 | 5 |
| 2 | 8.5400 | 10.34563 | 4 |
| 3 | 8.9712 | 9.84931 | 30 |
| 4 | 9.4917 | 9.31033 | 6 |
| 5 | 12.2731 | 7.20591 | 8 |
| 6 | 14.2000 | 6.23213 | 7 |
| 7 | 14.8293 | 5.96904 | 100 |
| 8 | 15.3400 | 5.77145 | 9 |
| 9 | 16.0514 | 5.51723 | 30 |
| 10 | 16.3600 | 5.41384 | 8 |
| 11 | 17.0775 | 5.18796 | 31 |
| 12 | 17.4651 | 5.07369 | 10 |
| 13 | 18.3418 | 4.83311 | 25 |
| 14 | 19.3099 | 4.59293 | 22 |
| 15 | 19.7703 | 4.48700 | 38 |
| 16 | 21.1340 | 4.20045 | 22 |
| 17 | 21.5207 | 4.12584 | 15 |
| 18 | 22.1600 | 4.00823 | 3 |
| 19 | 22.5560 | 3.93875 | 6 |
| 20 | 23.0743 | 3.85144 | 22 |
| 21 | 23.8286 | 3.73120 | 17 |
| 22 | 25.3114 | 3.51588 | 17 |
| 23 | 25.8400 | 3.44514 | 8 |
| 24 | 26.0800 | 3.41398 | 12 |
| 25 | 26.6000 | 3.34841 | 3 |
| 26 | 26.9400 | 3.30691 | 4 |
| 27 | 27.2305 | 3.27229 | 8 |
| 28 | 27.9737 | 3.18702 | 4 |
| 29 | 28.8733 | 3.08974 | 14 |
| 30 | 29.6000 | 3.01551 | 5 |
| 31 | 29.9400 | 2.98204 | 9 |
| 32 | 31.3543 | 2.85068 | 9 |
| 33 | 31.6800 | 2.82211 | 3 |
| 34 | 34.7180 | 2.58180 | 3 |
| 35 | 35.6950 | 2.51334 | 3 |
| 36 | 37.5325 | 2.39441 | 3 |

Anhydrous crystalline fexofenadine hydrochloride Form C according to the present invention is preferably further characterised as having a melting point in the range of about 191 to 196° C. (DSC; open capsule). More specifically, anhydrous crystalline fexofenadine hydrochloride Form C according to the present invention is preferably further characterised as having a melting point in the range of about 192 to 194° C. (DSC; open capsule) as shown in FIG. 2, which is distinguished from the prior art polymorphs as discussed above.

Anhydrous crystalline fexofenadine hydrochloride Form C according to the present invention is preferably more than about 99.5% w/w pure (peak area).

Anhydrous crystalline fexofenadine hydrochloride Form C according to the present invention can also be further characterised as having an infra red absorption spectrum, or substantially the same infra red absorption spectrum, as shown in FIG. 3.

The term "anhydrous" as used herein with reference to crystalline fexofenadine hydrochloride Form C denotes a moisture content thereof of less than about 0.5% by weight.

The present invention also provides hydrated crystalline fexofenadine acetate Forms D and E. Form D is crystalline fexofenadine acetate monohydrate. Form E is crystalline fexofenadine acetate dihydrate, which can be easily prepared on an industrial scale from fexofenadine free base substantially as hereinafter described in greater detail. Fexofenadine acetate dihydrate as provided by the present invention is crystalline, easy to filter and dry, and preparation of the acetate salt preferably removes most of the impurities that are otherwise difficult to remove.

Crystalline fexofenadine acetate dihydrate Form E according to the present invention can be characterised as having an infra red absorption spectrum, or substantially the same infra red absorption spectrum, as shown in FIG. 4.

The present invention also provides crystalline fexofenadine acetate dihydrate Form E having an X-ray diffraction pattern, or substantially the same X-ray diffraction pattern, as shown in FIG. 5. More particularly, crystalline fexofenadine acetate dihydrate Form E according to the present invention, can be characterised as having an X-ray diffraction pattern with characteristic peaks (2θ): 8.2266°, 9.3654°, 10.6929°, 11.1600°, 13.0400°, 13.4200°, 15.7473°, 16.4400°, 16.9785°, 17.5334°, 19.9728°, 20.7000°, 21.1236°, 23.0150° and 26.2977°.

Further characterising data for crystalline fexofenadine acetate dihydrate Form E according to the present invention as obtained by X-ray diffraction is shown in following table 2.

TABLE 2

| Peak No. | 2θ (deg) | d (A) | I/II |
|---|---|---|---|
| 1 | 6.5665 | 13.44981 | 8 |
| 2 | 7.9000 | 11.18226 | 6 |
| 3 | 8.2266 | 10.73904 | 29 |
| 4 | 8.9200 | 9.90573 | 7 |
| 5 | 9.3654 | 9.43561 | 21 |
| 6 | 9.8798 | 8.94546 | 8 |
| 7 | 10.6929 | 8.26699 | 43 |
| 8 | 11.1600 | 7.92200 | 13 |
| 9 | 13.0400 | 6.78379 | 31 |
| 10 | 13.4200 | 6.59255 | 26 |
| 11 | 14.5800 | 6.07054 | 7 |
| 12 | 14.9000 | 5.94088 | 10 |
| 13 | 15.3800 | 5.75653 | 10 |
| 14 | 15.7473 | 5.62308 | 22 |
| 15 | 16.4400 | 5.38768 | 33 |
| 16 | 16.9785 | 5.21799 | 100 |
| 17 | 17.5334 | 5.05408 | 30 |
| 18 | 18.5000 | 4.79213 | 6 |
| 19 | 18.7200 | 4.73631 | 10 |
| 20 | 19.3200 | 4.59055 | 24 |
| 21 | 19.9728 | 4.44196 | 63 |
| 22 | 20.7000 | 4.20753 | 32 |
| 23 | 21.1236 | 4.20249 | 66 |
| 24 | 21.8975 | 4.05569 | 16 |
| 25 | 22.4623 | 3.95497 | 21 |
| 26 | 23.0150 | 3.86123 | 25 |
| 27 | 23.5600 | 3.77313 | 5 |
| 28 | 23.8600 | 3.72636 | 6 |

TABLE 2-continued

| Peak No. | 2θ (deg) | d (A) | I/II |
|---|---|---|---|
| 29 | 24.7800 | 3.59006 | 10 |
| 30 | 25.1800 | 3.53393 | 16 |
| 31 | 25.7600 | 3.45566 | 7 |
| 32 | 26.2977 | 3.38621 | 29 |
| 33 | 27.1413 | 3.28284 | 11 |
| 34 | 27.7071 | 3.21708 | 5 |
| 35 | 28.7490 | 3.10281 | 6 |
| 36 | 30.1035 | 2.96621 | 8 |
| 37 | 30.9400 | 2.88790 | 6 |
| 38 | 31.3454 | 2.85147 | 14 |

Crystalline fexofenadine acetate monohydrate Form E is further characterised by a typical DSC thermograph showing three endotherms, as shown in FIG. 6. Two endotherms, the first one between 74° C. to 87° C. and the second one between 130° to 143° C. signify loss of the water molecules, and a sharp endotherm having onset at about 216° C. is the melting endotherm. Crystalline fexofenadine acetate dihydrate Form E according to the present invention is preferably, therefore, further characterised as having a melting point in the range of about 216 to 229° C. (DSC; open capsule) and DSC characteristics as shown in FIG. 6.

Crystalline fexofenadine acetate dihydrate Form E according to the present invention is preferably more than about 99.5% w/w pure (peak area).

The term "monohydrate" as used herein with reference to crystalline fexofenadine acetate Form D denotes a moisture content thereof in the range of about 3 to 5% by weight. The term "dihydrate" as used herein with reference to crystalline fexofenadine acetate Form E denotes a moisture content thereof in the range of about 6 to 8% by weight.

The present invention also provides crystalline fexofenadine free base monohydrate Form F.

Crystalline fexofenadine free base monohydrate Form F according to the present invention can be characterised as having an infra red absorption spectrum, or substantially the same infra red absorption spectrum, as shown in FIG. 7.

The present invention also provides crystalline fexofenadine free base monohydrate Form F having an X-ray diffraction pattern, or substantially the same X-ray diffraction pattern, as shown in FIG. 8. More particularly, crystalline fexofenadine free base monohydrate Form F according to the present invention, can be characterised as having an X-ray diffraction pattern with characteristic peaks (2θ): 3.6184°, 7.2914°, 9.5669°, 11.4946°, 11.9468°, 17.8400°, 18.2536°, 19.4768°, 21.6636°, 23.7517° and 25.6771°.

Further characterising data for crystalline fexofenadine free base monohydrate Form F according to the present invention as obtained by X-ray diffraction is shown in following table 3.

TABLE 3

| Peak No. | 2θ (deg) | d (A) | I/II |
|---|---|---|---|
| 1 | 3.6184 | 24.39878 | 53 |
| 2 | 7.2914 | 12.11420 | 12 |
| 3 | 9.5669 | 9.23732 | 22 |
| 4 | 11.4946 | 7.69214 | 26 |
| 5 | 11.9468 | 7.40198 | 13 |
| 6 | 13.2800 | 6.66173 | 7 |
| 7 | 13.6800 | 6.46783 | 16 |
| 8 | 14.0800 | 6.28497 | 9 |
| 9 | 16.0591 | 5.51460 | 11 |
| 10 | 17.8400 | 4.96791 | 76 |
| 11 | 18.2536 | 4.85626 | 100 |
| 12 | 19.4768 | 4.55395 | 53 |
| 13 | 20.5000 | 4.32890 | 21 |
| 14 | 20.8600 | 4.25500 | 20 |
| 15 | 21.3800 | 4.15267 | 16 |
| 16 | 21.6636 | 4.09894 | 34 |
| 17 | 22.5525 | 3.93935 | 18 |
| 18 | 23.7517 | 3.74310 | 23 |
| 19 | 25.6771 | 3.46663 | 22 |
| 20 | 26.5400 | 3.35584 | 16 |
| 21 | 26.8600 | 3.31658 | 15 |
| 22 | 27.7305 | 3.21441 | 10 |
| 23 | 28.5977 | 3.11888 | 12 |
| 24 | 30.2654 | 2.95071 | 10 |
| 25 | 31.1246 | 2.87119 | 14 |
| 26 | 32.3453 | 2.76556 | 10 |
| 27 | 35.8600 | 2.50215 | 7 |

Fexofenadine base monohydrate Form F is further characterised by a typical DSC thermograph showing two endotherms, as shown in FIG. 9. A broad endotherm between 70° C. to 102° C. signifies loss of the water molecule, and a sharp endotherm having onset at about 222° C. is the melting endotherm. There are two minor exotherms (between the two endotherms) likely to be indicative of phase transitions at high temperatures. Fexofenadine base monohydrate Form F according to the present invention is preferably, therefore, further characterised as having a melting point in the range of about 222 to 231° C. (DSC; open capsule) and DSC characteristics as shown in FIG. 9.

Crystalline fexofenadine free base monohydrate Form F according to the present invention is preferably more than about 99.5% w/w pure (peak area).

Fexofenadine has therapeutic utility as an $H_1$ receptor antagonist and is useful for administration to a patient to alleviate symptoms caused by histamine. As an antihistamine, fexofenadine is effective at relieving symptoms caused by airborne and contact inducers of histamine release. Such substances include pollen, spores, animal dander, industrial chemicals, dust and dust mites. Symptoms that can be alleviated by fexofenadine include bronchial spasms, sneezing, rhinorrhia, nasal congestion, lacrimation, redness, rash, urticaria and itch. The wording "anti-histaminic treatment" as used herein covers treatment of any of the above symptoms.

Fexofenadine polymorphs C, D, E or F, especially anhydrous crystalline fexofenadine hydrochloride Form C, as provided by the present invention, are useful for delivering fexofenadine to the gastrointestinal tract, mucus membranes, bloodstream and inflamed tissues of a patient suffering from inflammation caused by histamine. Fexofenadine Forms C, D, E or F, especially anhydrous crystalline fexofenadine hydrochloride Form C, are suitable for inclusion in pharmaceutical compositions for use in antihistaminic treatment and are also suitable for use in methods of treating a patient suffering from or susceptible to inflammation caused by histamine.

The present invention further provides, therefore, a pharmaceutically acceptable composition for antihistaminic treatment, which composition comprises a therapeutically effective amount of any of fexofenadine Forms C, D, E or F as described herein, especially anhydrous crystalline fexofenadine hydrochloride Form C, together with a pharmaceutically acceptable carrier, diluent or excipient therefor.

As used herein, the term "therapeutically effective amount" means an amount of any of fexofenadine Forms C, D, E or F which is capable of preventing, ameliorating or eliminating inflammation caused by histamine.

By "pharmaceutically acceptable composition" it is meant that the carrier, diluent or excipient is compatible with any of fexofenadine Forms C, D, E or F and not deleterious to a recipient thereof. Fexofenadine Forms C, D, E or F according to the present invention have been found to be suitable for formulation into stable solid compositions exhibiting good release properties.

The pharmaceutical compositions of the present invention may be administered in any suitable way and in any suitable form, for example orally (preferred) in the form of tablets, capsules, powders or liquid compositions (for example syrups), or for example parenterally in the form of conventional sterile solutions for injection, or inhalant or ophthalmic compositions.

The pharmaceutical compositions of the present invention may be prepared by conventional methods known in the art. For example, tablets may be prepared by mixing any of fexofenadine Forms C, D, E or F according to the present invention, with known adjuvants and/or diluents and subsequently compressing the mixture in a conventional tabletting machine. Examples of adjuvants or diluents can comprise corn starch, potato starch, talcum, magnesium stearate, gelatine, lactose, gums, and the like. Other adjuvants or additives such as colourings, aroma enhancers, preservatives and the like may be used provided that they are compatible with fexofenadine Forms C, D, E or F as described herein.

In liquid pharmaceutical compositions as provided by the present invention, any of fexofenadine Forms C, D, E or F, and any other solid excipients, can be dissolved or suspended in a liquid carrier such as water, vegetable oil, alcohol, polyethylene glycol, propylene glycol or glycerin. Liquid pharmaceutical compositions according to the present invention can where required also further comprise emulsifying agents, viscosity enhancing agents, sweetening agents, preservatives and buffers.

The particular dosage form of fexofenadine Forms C, D, E or F, especially anhydrous crystalline fexofenadine hydrochloride Form C, required for antihistaminic treatment as provided by the present invention will depend on the particular inflammation caused by histamine, and the symptoms and severity thereof. Dosage, routes of administration, and frequency of dosing are best decided by an attending physician.

The present invention further provides fexofenadine Forms C, D, E or F for use in the manufacture of a medicament for antihistaminic treatment.

The present invention also provides a method of antihistaminic treatment, which method comprises administering to a patient a therapeutically effective amount of any of fexofenadine Forms C, D, E or F, especially anhydrous crystalline fexofenadine hydrochloride Form C.

A further aspect of the present invention is a novel process for preparation of fexofenadine free base as a monohydrate by hydrolysis of a keto ester of formula III to the corresponding keto acid of formula II and subsequent reduction of the acid, suitably with sodium borohydride under aqueous or alcoholic conditions to give sodium salt of fexofenadine which is converted to the free base by pH adjustment.

There is provided by the present invention, therefore, a process of preparing fexofenadine, which process comprises reduction of a compound of formula (II)

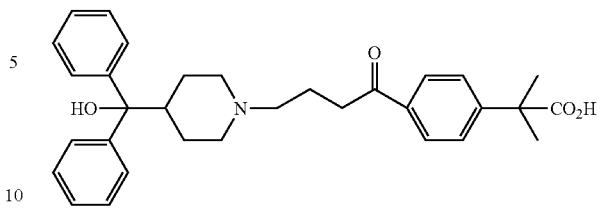

and isolation of fexofenadine free base monohydrate in crystalline form. Suitable reducing agents can include sodium borohydride, sodium cyanoborohydride, lithium aluminium hydride or the like. Preferably sodium borohydride is employed, and a compound of formula (II) can be reduced to initially yield the sodium salt of fexofenadine as indicated above, which is then converted to the free base by pH adjustment.

A process according to the present invention can further comprises, preparation of a compound of formula (II) by hydrolysis of a compound of formula (III)

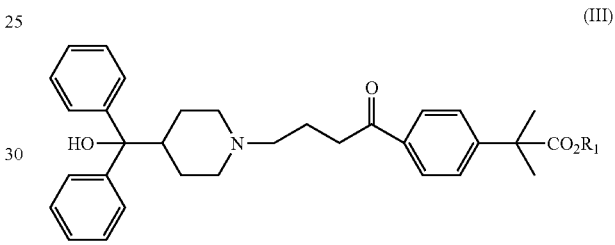

where $R_1$ is a suitable carboxy protecting group, such as $C_1$-$C_4$alkyl, in particular methyl.

The present invention further comprises a process of preparing fexofenadine, which process comprises hydrolysis of a compound of formula (III)

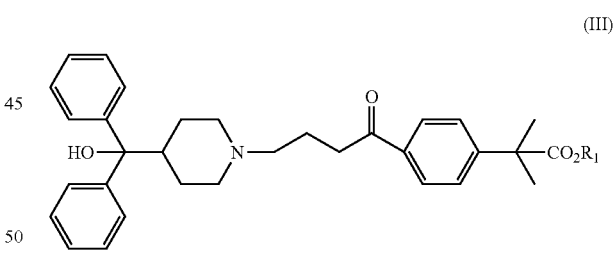

to yield a compound of formula (II)

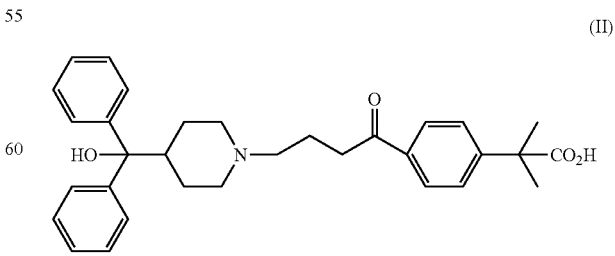

followed by reduction of a compound of formula (II) and isolation of fexofenadine free base monohydrate in crystalline form, and optionally converting said fexofenadine free base to a pharmaceutically acceptable salt.

In a process according to the present invention, it is preferred that a compound of formula (III) is prepared by the reaction of a protected derivative of formula (IV)

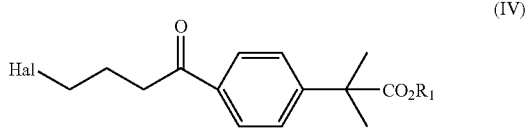

(IV)

where Hal is chloro, bromo or iodo, in particular chloro, and $R_1$ is a suitable carboxy protecting group, such as $C_1$-$C_4$alkyl, in particular methyl, as referred to above, with azacyclonal of formula (V)

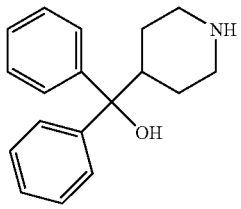

(V)

Typically a compound of formula (IV) is prepared from a protected derivative of formula (VI)

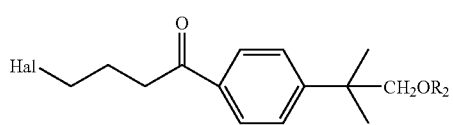

(VI)

where Hal is as defined above and $R_2$ is a suitable hydroxy protecting group, such as acetyl or benzyl, preferably acetyl, by a series of steps comprising deprotection, oxidation and subsequent re-protection prior to reaction with a compound of formula (V). Typically the reaction sequence can be represented as follows

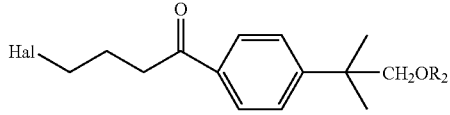

(VI)

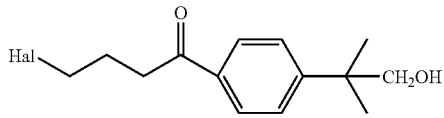

(VII)

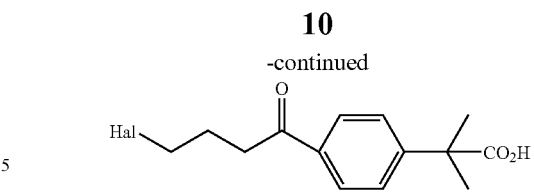

(VIII)

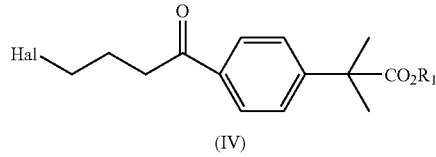

(IV)

A compound of formula (VI) is typically prepared by reaction of a protected derivative of formula (IX)

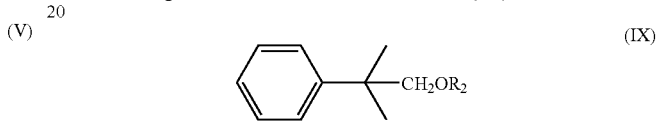

(IX)

where $R_2$ is a suitable hydroxy protecting group, such as acetyl or benzyl, preferably acetyl, as referred to above, with a halo compound of formula (X)

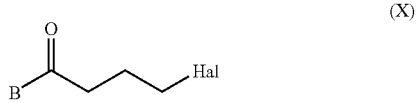

(X)

where Hal is as defined above and B is halo or hydroxy, typically halo and in particular chloro, suitably under the general conditions of a Friedel-Crafts acylation in the presence of a suitable Lewis acid. Suitable Lewis acids are well known in the art and include boron trichloride, aluminium chloride, titanium tetrachloride, boron trifluoride, tin tetrachloride, ferric chloride, cobalt (II) chloride and zinc chloride, with aluminium chloride being preferred.

A compound of formula (IX) is suitably prepared by protection of the corresponding hydroxy compound of formula (XI)

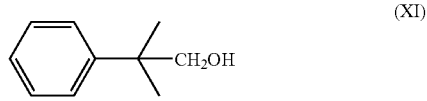

(XI)

by introduction of protecting group $R_2$, suitably by esterification.

A compound of formula (XI) is suitably prepared by esterification of a compound of formula (XII) and subsequent reduction of a compound of formula (XIII) according to the following reaction sequence

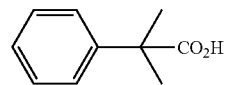

(XII)

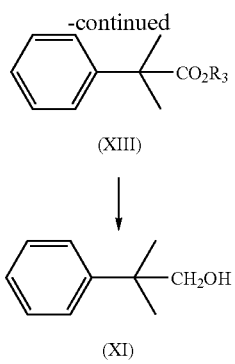

(XIII)

↓

(XI)

where $R_3$ is $C_1$-$C_4$alkyl, in particular methyl.

Suitably, a compound of formula (XII) is prepared by methylation of a compound of formula (XIV) and subsequent hydrolysis of a compound of formula (XV) according to the following reaction sequence

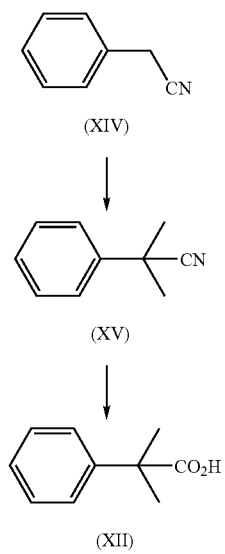

(XIV)

↓

(XV)

↓

(XII)

The above reaction steps typically yield fexofenadine free base monohydrate, which preferably can be further converted into a pharmaceutically acceptable salt. Suitable salts can include acetate and hydrochloride salts substantially as hereinbefore described and as represented by any of fexofenadine Forms C, D or E as provided by the present invention. Preferably a process substantially as hereinbefore described, therefore, further comprises treating fexofenadine free base, typically fexofenadine free base monohydrate Form F, with a pharmaceutically acceptable acid so as to yield a pharmaceutically acceptable salt, in particular treatment with hydrochloride acid and/or acetic acid to prepare any of anhydrous crystalline fexofenadine hydrochloride Form C, crystalline fexofenadine acetate monohydrate Form D or crystalline fexofenadine acetate dihydrate Form E as provided by the present invention.

In a particular embodiment, a process substantially as hereinbefore described further comprises reaction of fexofenadine free base monohydrate Form F as prepared thereby with hydrochloride acid so as to yield anhydrous crystalline fexofenadine hydrochloride Form C.

In an alternative embodiment, a process substantially as hereinbefore described further comprises reaction of fexofenadine free base monohydrate Form F as prepared thereby with acetic acid to yield crystalline fexofenadine acetate monohydrate Form D and subsequent conversion thereof (typically by exposing fexofenadine acetate monohydrate Form D to an atmosphere of sufficient humidity and for a sufficient amount of time) to crystalline fexofenadine acetate dihydrate Form E. Crystalline fexofenadine acetate dihydrate Form E can then be treated with hydrochloride acid so as to yield anhydrous crystalline fexofenadine hydrochloride Form C.

In a still further alternative embodiment, a process substantially as hereinbefore described further comprises reaction of fexofenadine free base monohydrate as prepared thereby with acetic acid to yield crystalline fexofenadine acetate dihydrate Form E. Crystalline fexofenadine acetate dihydrate Form E can then be treated with hydrochloride acid so as to yield anhydrous crystalline fexofenadine hydrochloride Form C.

According to the present invention there is further provided a process of preparing crystalline fexofenadine acetate monohydrate Form D from crystalline fexofenadine free base monohydrate Form F. Typically, this process comprises dissolving crystalline fexofenadine free base monohydrate Form F in a first aqueous solution (such as aqueous sodium hydroxide) and converting the free carboxyl group of fexofenadine to an alkali metal salt functionality (such as the sodium salt), quenching the resulting aqueous solution into a further aqueous solution containing an excess of acetic acid and effecting precipitation of crystalline fexofenadine acetate monohydrate Form D therefrom.

According to the present invention, there is still further provided a process of preparing crystalline fexofenadine acetate dihydrate Form E from crystalline fexofenadine acetate monohydrate Form D, which comprises exposing fexofenadine acetate monohydrate Form D to an atmosphere of sufficient humidity and for a sufficient amount of time to yield crystalline fexofenadine acetate dihydrate Form E.

According to the present invention there is further provided a process of preparing crystalline fexofenadine acetate dihydrate Form E from crystalline fexofenadine free base monohydrate Form F. Typically, this process comprises dissolving crystalline fexofenadine free base monohydrate Form F in a first aqueous solution (such as aqueous sodium hydroxide) and converting the free carboxyl group of fexofenadine to an alkali metal salt functionality (such as the sodium salt), quenching the resulting aqueous solution into a further aqueous solution containing an excess of acetic acid and effecting precipitation of crystalline fexofenadine acetate dihydrate Form E therefrom.

According to the present invention there is further provided a process of preparing anhydrous crystalline fexofenadine hydrochloride Form C from crystalline fexofenadine free base monohydrate Form F. Typically this process comprises reaction of crystalline fexofenadine free base monohydrate Form F with hydrochloride acid. Preferably, crystalline fexofenadine free base monohydrate Form F is suspended in a first organic solvent medium and hydrochloric acid (typically as dry hydrochloric acid gas) is added thereto; concentrating to obtain a residue; adding the residue to a second organic solvent medium and effecting precipitation of anhydrous crystalline fexofenadine hydrochloride Form C therefrom. Typically, the first organic solvent medium can comprise a ketone as the solvent, such as acetone; alternatively the first organic solvent medium can comprise THF. Typically, the second organic solvent medium can comprise a mixture of an ester and an alcohol, such as isopropanol and ethyl acetate.

According to the present invention there is further provided a process of preparing anhydrous crystalline fexofenadine hydrochloride Form C from crystalline fexofenadine acetate dihydrate Form E, wherein crystalline fexofenadine acetate dihydrate Form E is prepared from crystalline fexofenadine free base monohydrate Form F. Crystalline fexofenadine acetate dihydrate Form E can be prepared directly from crystalline fexofenadine free base monohydrate Form F, or via crystalline fexofenadine acetate monohydrate Form D substantially as hereinbefore described. Typically this process comprises reaction of crystalline fexofenadine acetate dihydrate Form E with hydrochloride acid. Preferably, crystalline fexofenadine acetate dihydrate Form E is suspended in a first organic solvent medium and hydrochloric acid (typically as dry hydrochloric acid gas) is added thereto; concentrating to obtain a residue; adding the residue to a second organic solvent medium and effecting precipitation of anhydrous crystalline fexofenadine hydrochloride Form C therefrom. Typically, the first organic solvent medium can comprise a ketone as the solvent, such as acetone; alternatively the first organic solvent medium can comprise THF. Typically, the second organic solvent medium can comprise a mixture of an ester and an alcohol, such as isopropanol and ethyl acetate.

In each of the above processes for the preparation of anhydrous crystalline fexofenadine hydrochloride Form C, this is prepared from either crystalline fexofenadine free base monohydrate Form F or crystalline fexofenadine acetate dihydrate Form E, without going through hydrated fexofenadine hydrochloride.

The present invention further provides use of crystalline fexofenadine free base monohydrate Form F substantially as hereinbefore described, for preparation of anhydrous fexofenadine hydrochloride (any form). There is also provided by the present invention use of crystalline fexofenadine acetate dihydrate Form E substantially as hereinbefore described, for preparation of anhydrous fexofenadine hydrochloride (any form).

There is further provided by the present invention any of anhydrous crystalline fexofenadine hydrochloride Form C, crystalline fexofenadine acetate monohydrate Form D, crystalline fexofenadine acetate dihydrate Form E and crystalline fexofenadine free base monohydrate Form F, prepared by a process substantially as hereinbefore described.

BRIEF DESCRIPTION OF THE DRAWINGS

The present invention will now be further illustrated by the following Figures, Intermediates and Examples, which do not limit the scope of the invention in any way. In the experimental of the following Intermediates, where reactants or reagents are described as "above", this means they are employed in the amounts specified therefor in the foregoing lists of reactants and reagents.

INTERMEDIATES

Intermediate 1

Preparation of 2,2-dimethyl-2-phenyl-acetic acid

Figure 1:
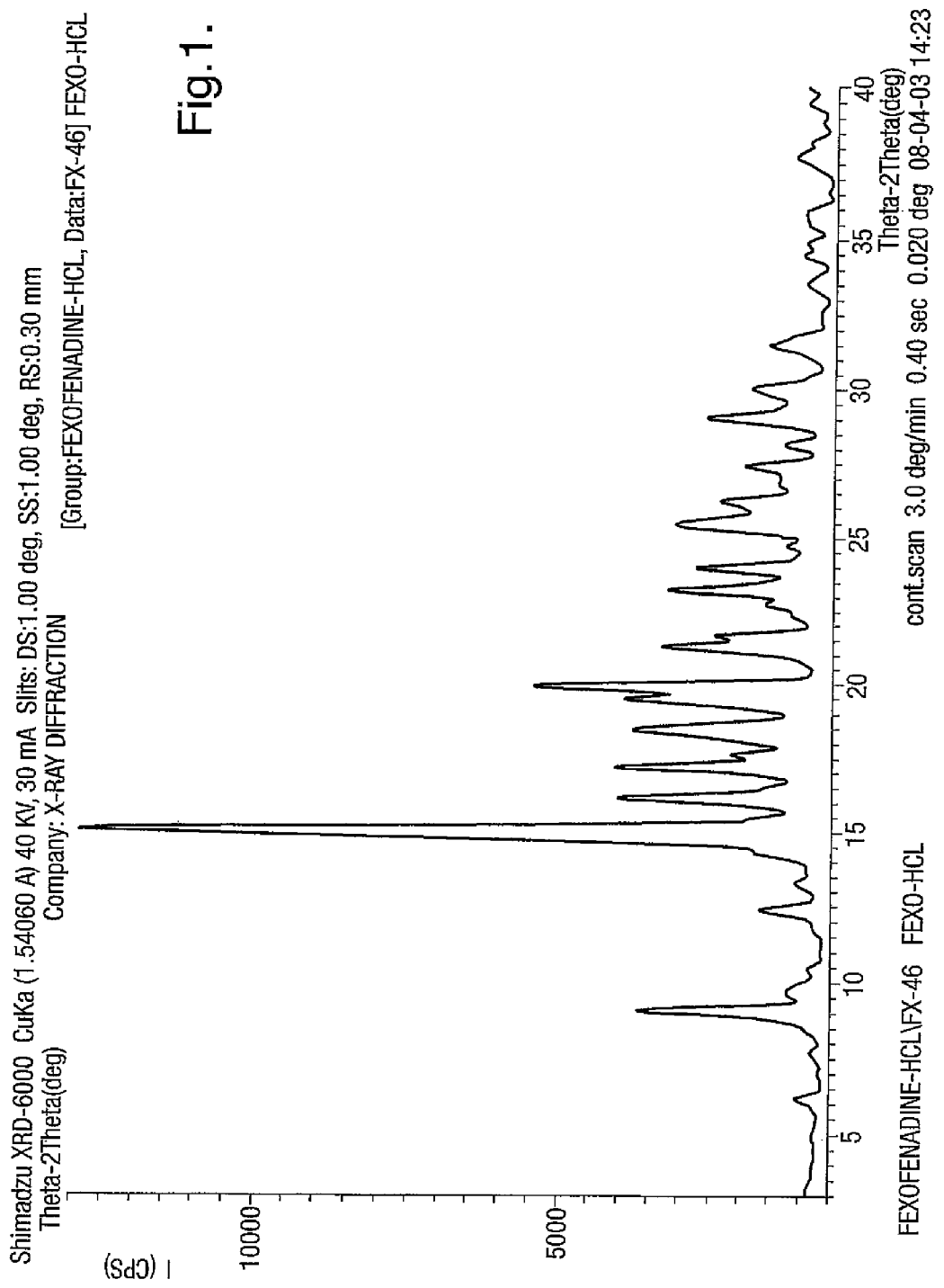
FIG. 1 is a PXRD pattern of anhydrous fexofenadine hydrochloride.
Figure 2:
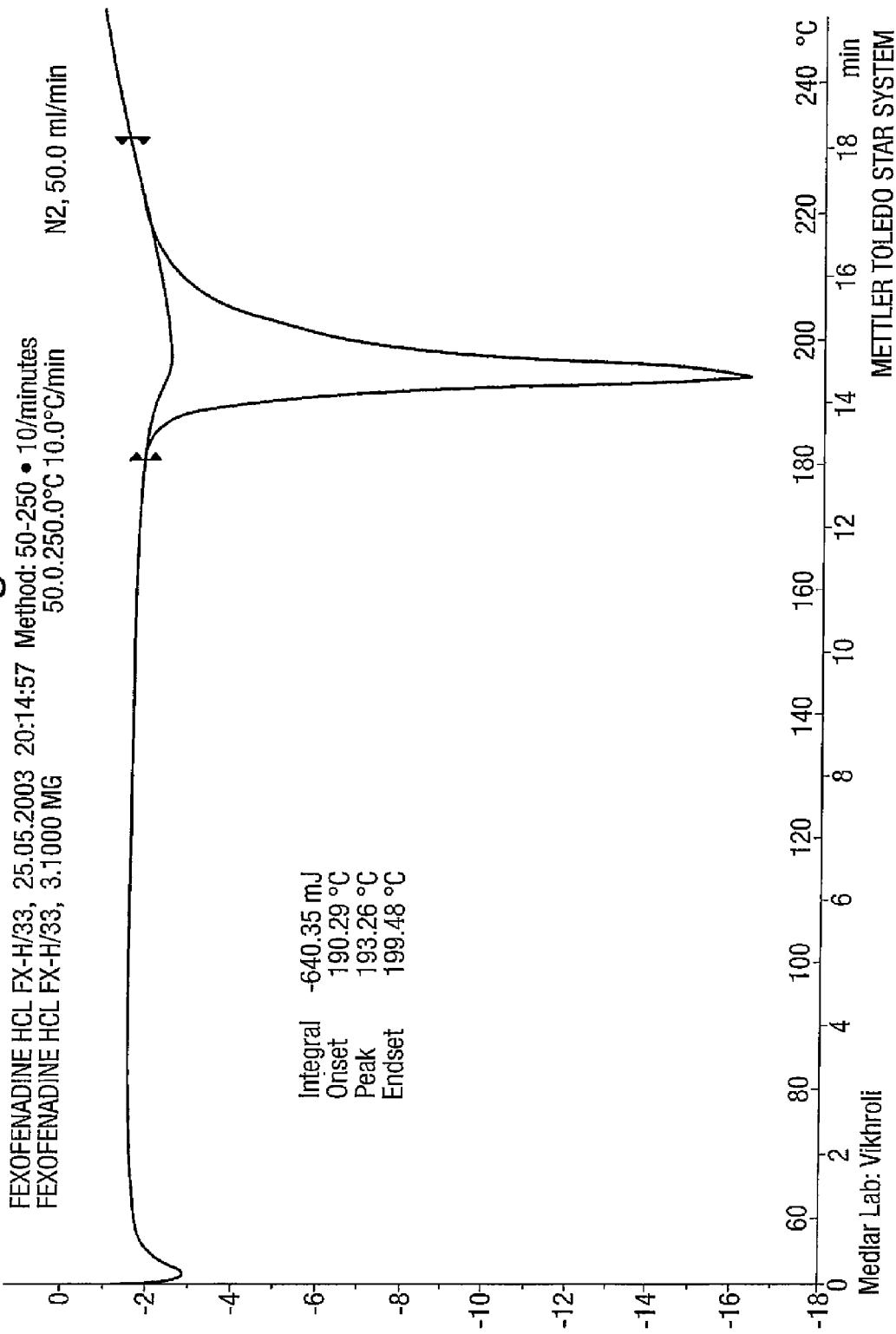
FIG. 2 is a DSC pattern of anhydrous fexofenadine hydrochloride.
Figure 3:
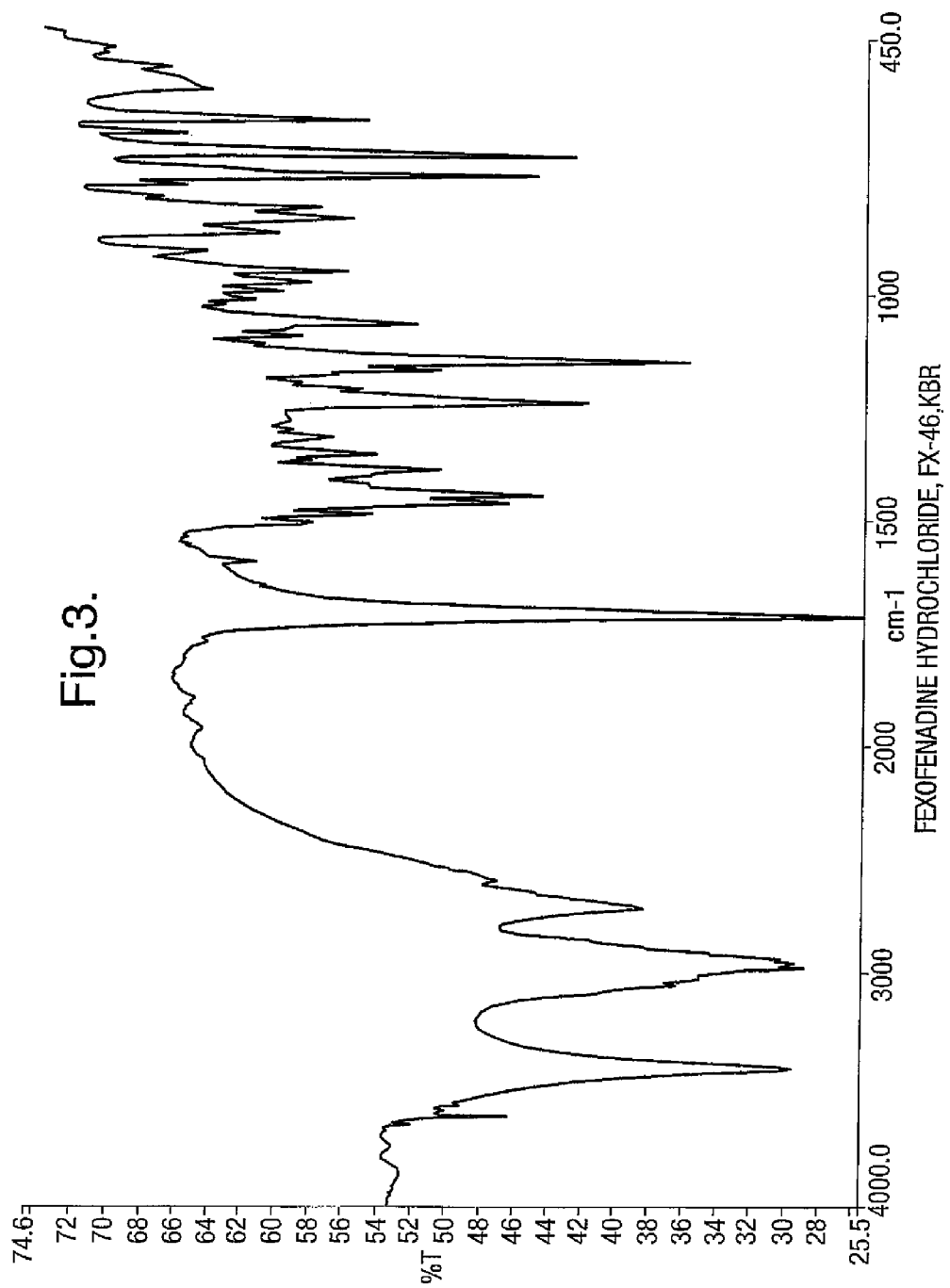
FIG. 3 is an IR spectrum of anhydrous fexofenadine hydrochloride.
Figure 4:
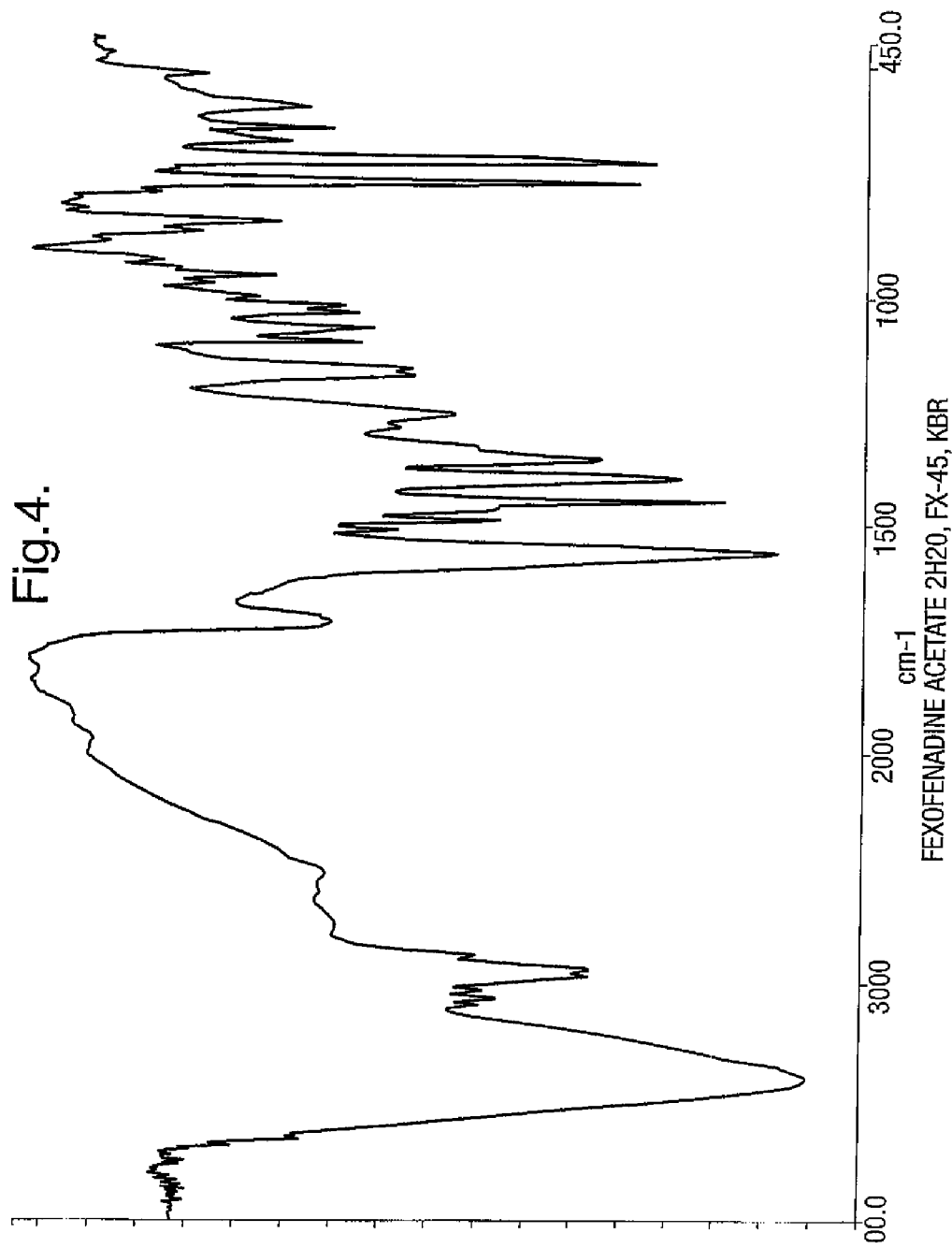
FIG. 4 is an IR spectrum of fexofenadine acetate dihydrate.

Benzyl cyanide (0.5 kg), potassium hydroxide (1.4 kg) and DMSO (2.5 ltr) were initially charged to a reactor and dimethyl sulphate (1.20 kg) was slowly added thereto over a period of one hour. The mixture was stirred for 3-4 hours at room temperature. The mass was slowly quenched in water with stirring. The pH was adjusted to 1-2 with conc HCl. The solution was filtered, the solids washed with water and the resulting material was dried under vacuum in an oven. The resulting product was suspended in water (3.0 ltr), sodium hydroxide (0.5 kg) added thereto and the mixture refluxed for 6 hours. After completion of the reaction, the reaction mass was cooled to room temperature and acidified with HCl to pH 2-3. The resulting precipitated material was filtered, washed with water and dried to obtain the title product.

Intermediate 2

Preparation of methyl-2,2-dimethyl-2-phenyl acetate

Methanol (2.5 ltr), 2,2-dimethyl-2-phenyl-acetic acid (Intermediate 1) (0.5 kg), and conc. sulphuric acid (50 ml) were charged to a reactor at room temperature. The temperature was raised to reflux and maintained for 12 hours. The pH was adjusted to 7-8 using aqueous ammonia and the methanol concentrated completely. The reaction mass was quenched in water (1 ltr) and extracted with MDC (750 ml). The MDC layer was dried over sodium sulphate and concentrated to obtain 500 gms of the title compound as an oil having 98% purity.

Intermediate 3

Preparation of 2-methyl-2-phenyl-propanol

Methyl-2,2-dimethyl-2-phenyl acetate (Intermediate 2) (0.5 kg), and THF (2.5 ltr) were charged to a reactor, and sodium borohydride (100 gms) was added in lots. The mixture was stirred at room temperature for 5 hours. After completion of the reaction, the pH was adjusted to 3-4 with HCl, the inorganics filtered and the filtrate concentrated and stripped with toluene (50 ml) to obtain the title compound as an oil weighing 400 gms.

Intermediate 4

Preparation of methyl 2-methyl-2-phenyl-propanoate 2-methyl-2-phenyl-propanol (Intermediate 3) (0.5 kg) and pyridine (268 ml) were charged to a reactor and chilled to 0° C. Acetic anhydride (680 gms) was slowly added through a dropper at 10-20° C. The mixture was stirred for 2 hours at 10-20° C. Ethyl acetate (1.5 ltr) was added and chilled water (2 ltrs) was slowly added through a dropper at 10-20° C. The mixture was stirred for ½ hr. The ethyl acetate layer was separated and 10% chilled dilute HCl was added. The ethyl acetate layer was then washed with sodium bicarbonate until a pH of 7 was obtained. The ethyl acetate layer was dried with sodium sulphate and concentrated under vacuum. The resulting oil was distilled under vacuum (15 mm of Hg), at 80-100° C.

Intermediate 5

Preparation of methyl-2-[4-(4-chloro-butyryl-)phenyl]-2-methyl-propanoate

MDC (600 ml) and aluminium chloride (347 gms) were charged to a reactor and chilled to −10° C. Methyl-2-methyl-2 phenyl-propanoate (Intermediate 4) (500 gms) was dissolved in MDC (650 ml) and added slowly through a dropper at −10 to 0° C. to obtain mixture A. MDC (600 ml) and aluminium chloride (520 gms) were charged to a different reactor, and chilled to −10° C. 4-chloro butyryl chloride (550 gms) was dissolved in MDC (650 ml) and added slowly through a dropper at −10 to 0° C. to obtain mixture B. Both mixtures A and B were stirred for 45 minutes at −10 to 0° C. separately. Mixture A was added to mixture B slowly at −10 to 0° C. and the reaction monitored by GC for completion (24 hours). The mass was quenched slowly in conc. HCl (1 ltr) at 10-20° C. and stirred for 30 minutes. The MDC layer was separated and the aqueous layer extracted with MDC (500 ml). The combined MDC layer was dried over sodium sulfate and concentrated under vacuum to obtain 880 gms of the title compound as an oil.

Intermediate 6

Preparation of 2-[4-(4-chloro-butyryl)phenyl]-2-methyl-propanol

Methyl-2-[4-(4-chlorobutyryl)-phenyl]-2-methyl propanoate (Intermediate 5) (0.5 kg) and methanol (750 ml) were charged to a reactor and cooled to 10-20° C. Conc. HCl (250 ml) was added at 10-20° C. and stirred for 24 hours at room temperature. The reaction was monitored by TLC for completion. The pH of the reaction mass was adjusted to 7-8 with aqueous ammonia at 20-30° C. and the methanol was concentrated. The reaction mixture was quenched in water (1 ltr) and extracted with MDC (500 ml). The MDC layer was dried over sodium sulphate and concentrated to obtain 400 gms of the title compound as an oil.

Intermediate 7

Preparation of 2-[4-(4-chloro-butyryl-phenyl]-2-methyl-propanoic acid

Acetic acid (1.0 ltr) and acetone (1.0 ltr) were charged to a reactor. Potassium permanganate (464 gms) was charged to the reactor and the mass chilled to 0° C. 2-[4-(4-chlorobutyrl) phenyl])-2-methyl propanol (Intermediate 6) (0.5 kg) was dissolved in acetone (500 ml) and added slowly at 0° C.-10° C. The reaction mass was stirred at 10-20° C. for 15 hours. MDC (1 ltr) was added to the reaction mass. Sodium metabisulphite (250 gms) was dissolved in water (1½ ltr) and added to the reaction mass at 10-20° C. The colour of the reaction mass changed from brown to colourless. The MDC layer was separated and the aqueous layer was extracted with MDC (250 ml). The MDC layer was separated. The MDC layers were combined and dried over sodium sulphate. The MDC layer was concentrated to obtain 575 gms of crude oil. Potassium carbonate (232 gms) was dissolved in water (1 ltr) and added to the oil. The pH was 9-10. Ethyl acetate was chilled to 10° C. and 6 extractions (each 300 ml) of the aqueous layer were carried out with the chilled ethyl acetate. MDC (750 ml) was added to the aqueous solution. The pH of the aqueous layer was adjusted to 5 using dilute HCl in biphase. The MDC layer was separated and MDC (250 ml) was again employed to extract the aqueous layer. The MDC layer was separated. The MDC layers were combined and dried over sodium sulphate. The MDC was concentrated to obtain the title compound as an oil weighing 265 gms.

Intermediate 8

Preparation of methyl 2-[4-(4-chloro-butyryl)phenyl)]-2-methyl-propionate

Acetone (3.5 ltr), 2-[4-(4-chlorobutyryl)phenyl]-2 methyl propanoic acid (Intermediate 7) (0.5 kg) and anhydrous potassium carbonate (232 gms) were charged to a reactor and chilled to 10° C. Dimethyl sulphate (234 gms) was slowly added at 10-20° C. and the reaction mixture stirred at room temperature for 5 hours. The mixture was heated to 35-40° C. for 2 hours until the reaction was complete. The reaction mass was filtered and the acetone concentrated. MDC (600 ml) was added, the MDC layer separated and washed with water. The MDC layer was dried over sodium sulphate and the MDC concentrated to obtain the title compound as a light brown oil weighing 460 gms.

Intermediate 9

Preparation of 4-[4-(4-hydroxy diphenyl methyl)-1-piperidinyl]-1-oxybutyl]-α,α-dimethyl benzene acetic, methyl ester Methyl-2-[4-(4-chloro-1-oxo-butyl]phenyl]-2-methyl propionate (Intermediate 8) (0.5 kg), anhydrous potassium carbonate (349 gms), potassium iodide (9.7 gms), azacyclonol (328 gms), MIBK (2.0 ltr) and DMF (0.5 ltr) were charged to a reactor. A Dean and Stark arrangement for water removal was set up (about 10 ml of water separated out). The reaction mass was heated for 18 hours at 120° C. The reaction mass was then cooled to room temperature and the inorganics filtered. The MIBK layer was then washed with water. The MIBK was concentrated to obtain 800 gms of oil. 2 volumes of alcohol were charged and stirred at 40° C. for 2 hours, followed by cooling to 5° C. The solids were filtered and dried to obtain the title compound.

EXAMPLES

Example 1

Preparation of Fexofenadine Free Base Monohydrate

4-[4-(4-hydroxydiphenyl methyl)-1-piperidinyl]-1-oxobutyl]-α,α-dimethyl benzene acetic, methyl ester (20 gms) (Intermediate 9) was suspended in isopropanol (75 ml) and 25% sodium hydroxide solution (4 ml) was added. The mixture was refluxed for 5 hours. The pH of the reaction mixture was adjusted to 5.5-6 with dilute acetic acid. The precipitated product was filtered and dried to give 4-[4-(4-hydroxydiphenyl methyl)-1-piperidinyl]-1-oxo-butyl]-α,α-dimethyl benzene acetic acid.

The above product was suspended in methanol and sodium borohydride (0.75 gms) was added slowly over 2 hours. The mixture was stirred at 30° C. for 10 hours. The pH of the mixture was adjusted to 5.5 to 6 with dilute acetic acid. The precipitated product was filtered and dried to give fexofenadine base monohydrate.

Example 2

Preparation of Fexofenadine Acetate Monohydrate

Fexofenadine base was suspended in a 5% aqueous sodium hydroxide solution (250 ml). The mixture was stirred to get a clear solution. The clear solution was then quenched at room temperature into a mixture of acetic acid (35 gms) in water (250 ml). The mixture was stirred for 1 hour at room temperature and the solids filtered and washed with water to obtain a neutral pH. The solids were dried under vacuum at 600-70° C. until the moisture content was between 3.5% to 4.2%.

Example 3

Preparation of Fexofenadine Acetate Dihydrate

Fexofenadine base was suspended in a 5% aqueous sodium hydroxide solution (250 ml). The mixture was stirred to get a clear solution. The clear solution was then quenched at room temperature into a mixture of acetic acid (35 gms) in water (250 ml). The mixture was stirred for 1 hour at room temperature and the solids filtered and washed with water to obtain a neutral pH. The solids were dried under vacuum at 60°-70° C. until the moisture content was between 6.5% to 7.7%.

Example 4

Preparation of Fexofenadine Acetate Dihydrate

Fexofenadine acetate monohydrate was exposed to an atmosphere of 60% relative humidity for 4 hours at 30° C. to give fexofenadine acetate dihydrate having a moisture content of 6.9-7.5%.

Example 5

Preparation of Anhydrous Fexofenadine Hydrochloride (i) Process from Fexofenadine Acetate Fexofenadine acetate (25 gms) was suspended in acetone (100 ml). Dry hydrochloric acid gas was bubbled into the suspension maintaining the temperature in the range of 25° C. to 30° C. The pH of the mixture was adjusted to between 1-2 to get a clear solution. The clear acetone solution was concentrated under vacuum to get a residue. The residue was stripped with acetone followed by toluene to remove traces of hydrogen chloride.

To the residue was added 250 ml of a mixture of isopropanol and ethyl acetate (1:9) and stirred at about 25° C. for 3-4 hours until the precipitation was complete. The reaction mixture was cooled to 5° C., the solids filtered. The product was dried under vacuum at 60° C.-70° C. until the moisture content was less than 0.5%.

(ii) Process from Fexofenadine Base

Fexofenadine base (25 gms) was suspended in acetone (100 ml). Dry hydrochloric acid gas was bubbled into the suspension maintaining the temperature in the range of 25° C. to 30° C. The pH of the mixture was adjusted to between 1-2 to get a clear solution. The clear acetone solution was concentrated under vacuum to get a residue. The residue was stripped with acetone followed by toluene to remove traces of hydrogen chloride.

To the residue was added 250 ml of a mixture of isopropanol and ethyl acetate (1:9) and stirred at about 25° C. for 3-4 hours until the precipitation was complete. The reaction mixture was cooled to 5° C., the solids filtered. The product was dried under vacuum at 60° C.-70° C. until the moisture content was less than 0.5%.

(iii) Process from Fexofenadine Acetate

Fexofenadine acetate (25 gms) was suspended in tetrahydrofuran (75 ml). Dry hydrochloric acid gas was bubbled into the suspension maintaining the temperature in the range of 25° C. to 30° C. The pH of the mixture was adjusted between 1-2 to get a clear solution. The clear THF solution was concentrated under vacuum to get a residue. The residue was stripped with THF followed by toluene to remove traces of hydrogen chloride.

To the residue was added 250 ml of a mixture of isopropanol and ethyl acetate (1:9) and stirred at about 25° C. for 3-4 hours until the precipitation was complete. The reaction mixture was cooled to 5° C., the solids filtered. The product was dried under vacuum at 60° C.-70° C. until the moisture content was less than 0.5%.

(iv) Process from Fexofenadine Base

Fexofenadine base (25 gms) was suspended in tetrahydrofuran (70 ml). Dry hydrochloric acid gas was bubbled into the suspension maintaining the temperature in the range of 25° C. to 30° C. The pH of the mixture was adjusted to between 1-2 to get a clear solution. The clear THF solution was concentrated under vacuum to get a residue. The residue was stripped with THF followed by toluene to remove traces of hydrogen chloride.

To the residue was added 250 ml of a mixture of isopropanol and ethyl acetate (1:9) and stirred at about 25° C. for 3-4 hours until the precipitation was complete. The reaction mixture was cooled to 5° C., the solids filtered. The product was dried under vacuum at 60° C.-70° C. until the moisture content was less than 0.5%.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Description of Related Art is not an admission that it is prior art to the present

Figure 7:
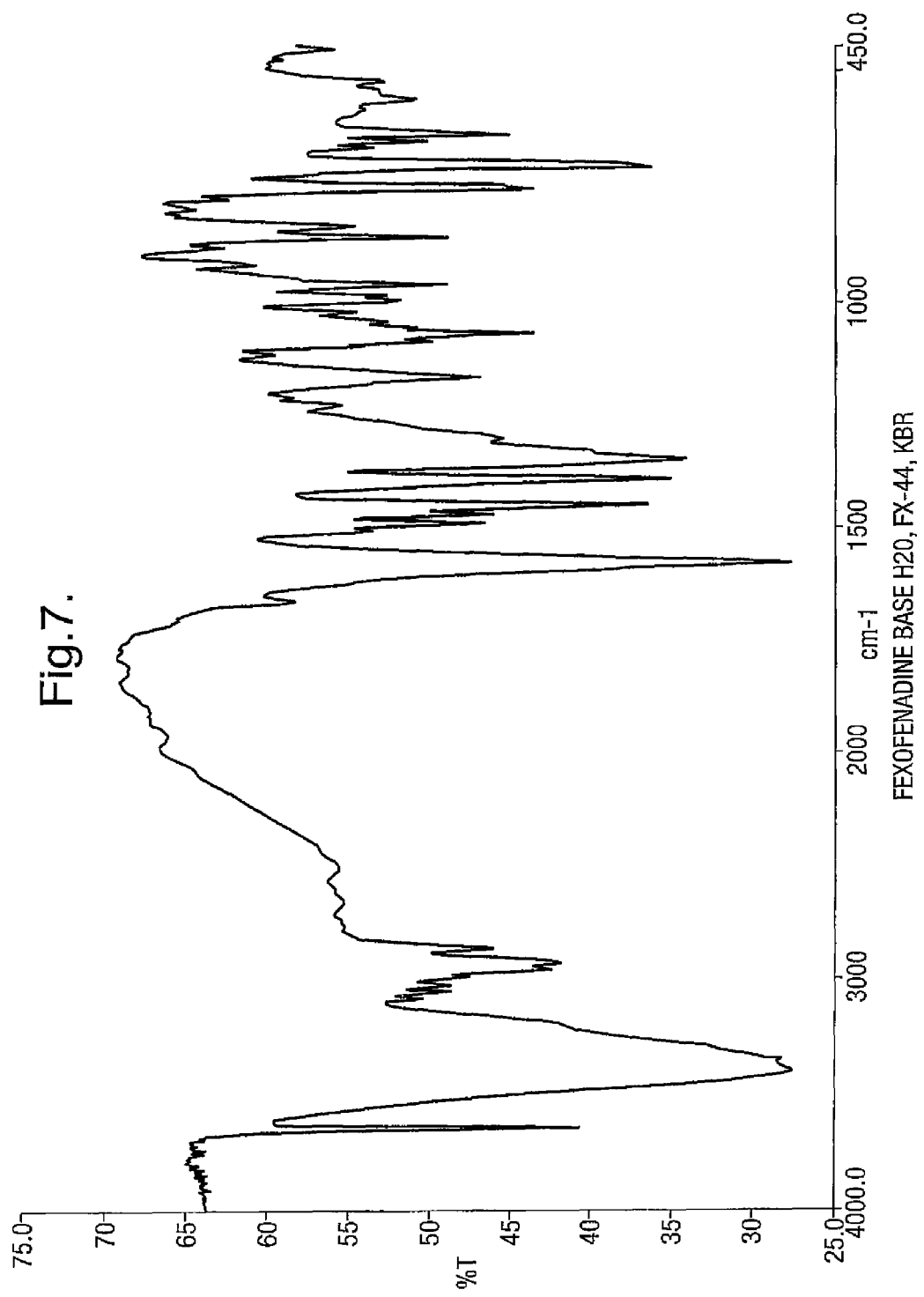
FIG. 7 is an IR spectrum of fexofenadine base monohydrate.

The invention claimed is:

1. Crystalline fexofenadine free base monohydrate Form F characterised as having an infra red absorption spectrum, or substantially the same infra red absorption spectrum, as shown in FIG. 7.

Figure 8:
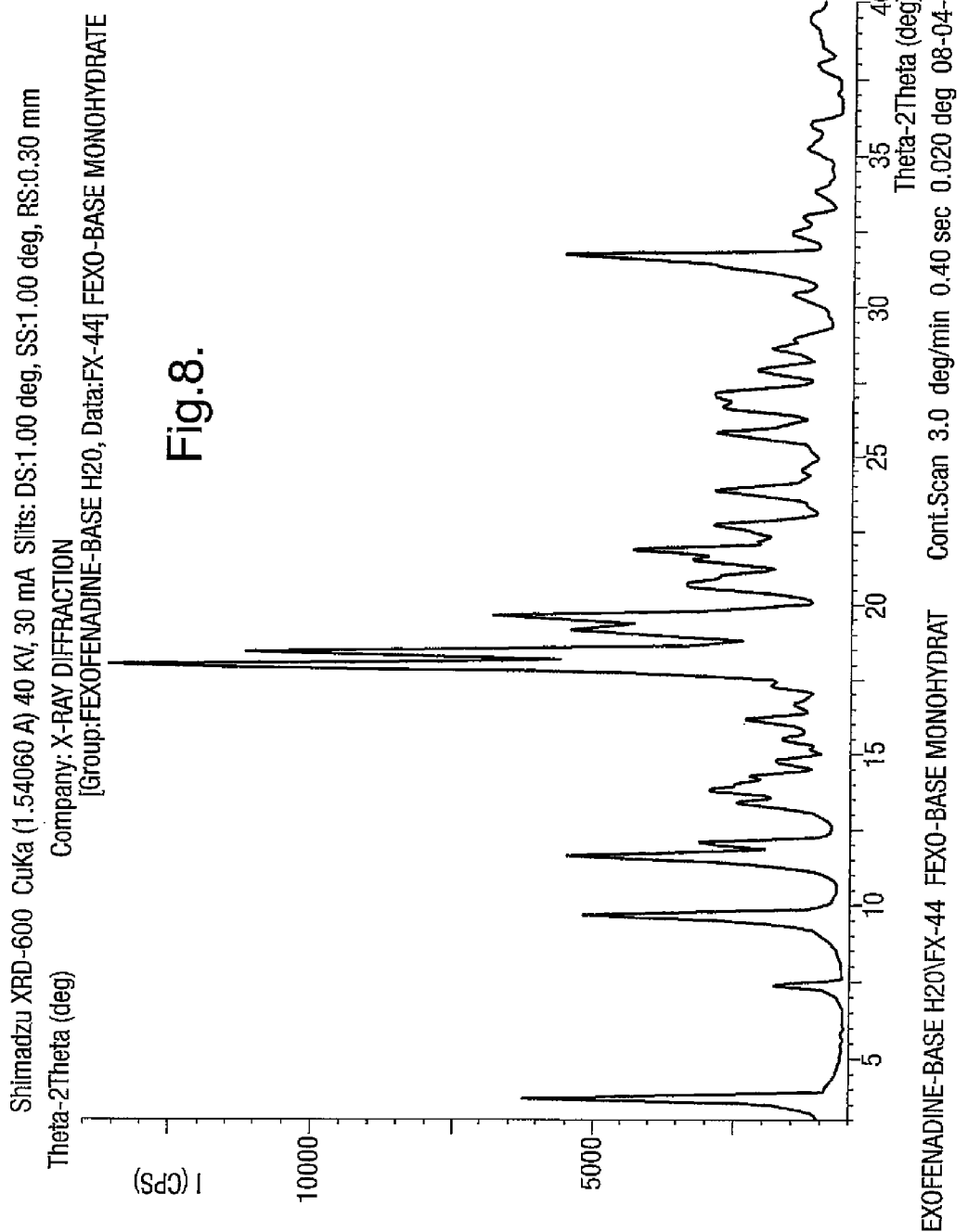
FIG. 8 is a PXRD pattern of fexofenadine base monohydrate.

2. Crystalline fexofenadine free base monohydrate Form F having an X-ray diffraction pattern, or substantially the same X-ray diffraction pattern, as shown in FIG. 8.

3. Crystalline fexofenadine free base monohydrate Form F characterised as having an X-ray diffraction pattern with characteristic peaks (2θ): 3.6184°, 7.2914°, 9.5669°, 11.4946°, 11.9468°, 17.8400°, 18.2536°, 19.4768°, 21.6636°, 23.7517° and 25.6771°.

4. Fexofenadine free base monohydrate Form F according to claim 2 characterised as having a melting point in the range of about 222 to 231° C.

5. Fexofenadine free base monohydrate Form F according to claim 2, which is more than about 99.5% w/w pure.

Figure 9:
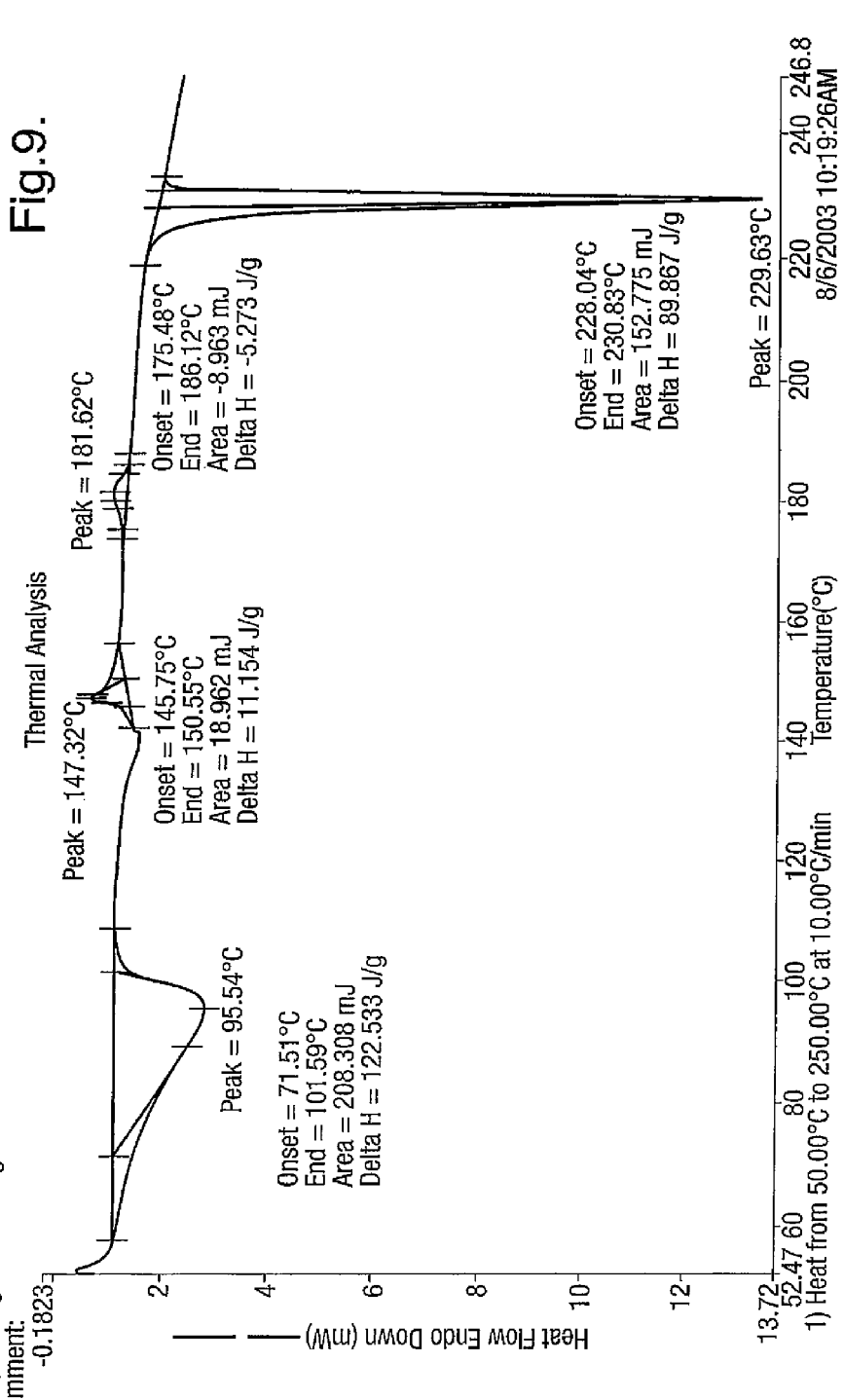
FIG. 9 is a DSC pattern of fexofenadine base monohydrate.

6. Fexofenadine free base monohydrate Form F having DSC characteristics as shown in FIG. 9.

7. Fexofenadine free base monohydrate Form F according to claim 1 having an X-ray diffraction pattern, or substantially the same X-ray diffraction pattern, as shown in FIG. 8 and DSC characteristics as shown in FIG. 9.

8. Crystalline fexofenadine free base monohydrate Form F according to claim 2 characterised as having an X-ray diffraction pattern with characteristic peaks (2θ): 3.6184°, 7.2914°, 9.5669°, 11.4946°, 11.9468°, 17.8400°, 18.2536°, 19.4768°, 21.6636°, 23.7517° and 25.6771° and an infra red absorption spectrum, or substantially the same infra red absorption spectrum, as shown in FIG. 7.

9. Crystalline fexofenadine free base monohydrate Form F according to claim 2 characterised as having an X-ray diffraction pattern with characteristic peaks (2θ) as presented in Table 3.

10. A composition comprising crystalline fexofenadine free base monohydrate Form F according to claim 2 and a pharmaceutically acceptable solid carrier, adjuvant, diluent, or excipient.

11. The composition of claim 10 wherein the composition further comprises corn starch, potato starch, talcum, magnesium stearate, gelatine, lactose, gums, or combinations thereof.

12. The composition of claim 10 wherein the carrier comprises water, vegetable oil, alcohol, polyethylene glycol, propylene glycol, glycerin, or combinations thereof.

13. A process comprising contacting the crystalline fexofenadine free base monohydrate form F according to claim 2 with hydrochloric acid to form the pharmaceutically acceptable salt of anhydrous crystalline fexofenadine hydrochloride Form C characterised as having an X-ray diffraction pattern, or substantially the same X-ray diffraction pattern, as shown in FIG. 1.

14. A process comprising contacting the crystalline fexofenadine free base monohydrate Form F according to claim 2 with acetic acid to form the pharmaceutically acceptable salt of crystalline fexofenadine acetate monohydrate Form D.

15. A process according to claim 14 further comprising exposing fexofenadine acetate monohydrate Form D to an atmosphere of sufficient humidity and for a sufficient amount of time to yield crystalline fexofenadine acetate dihydrate Form E.

Figure 5:
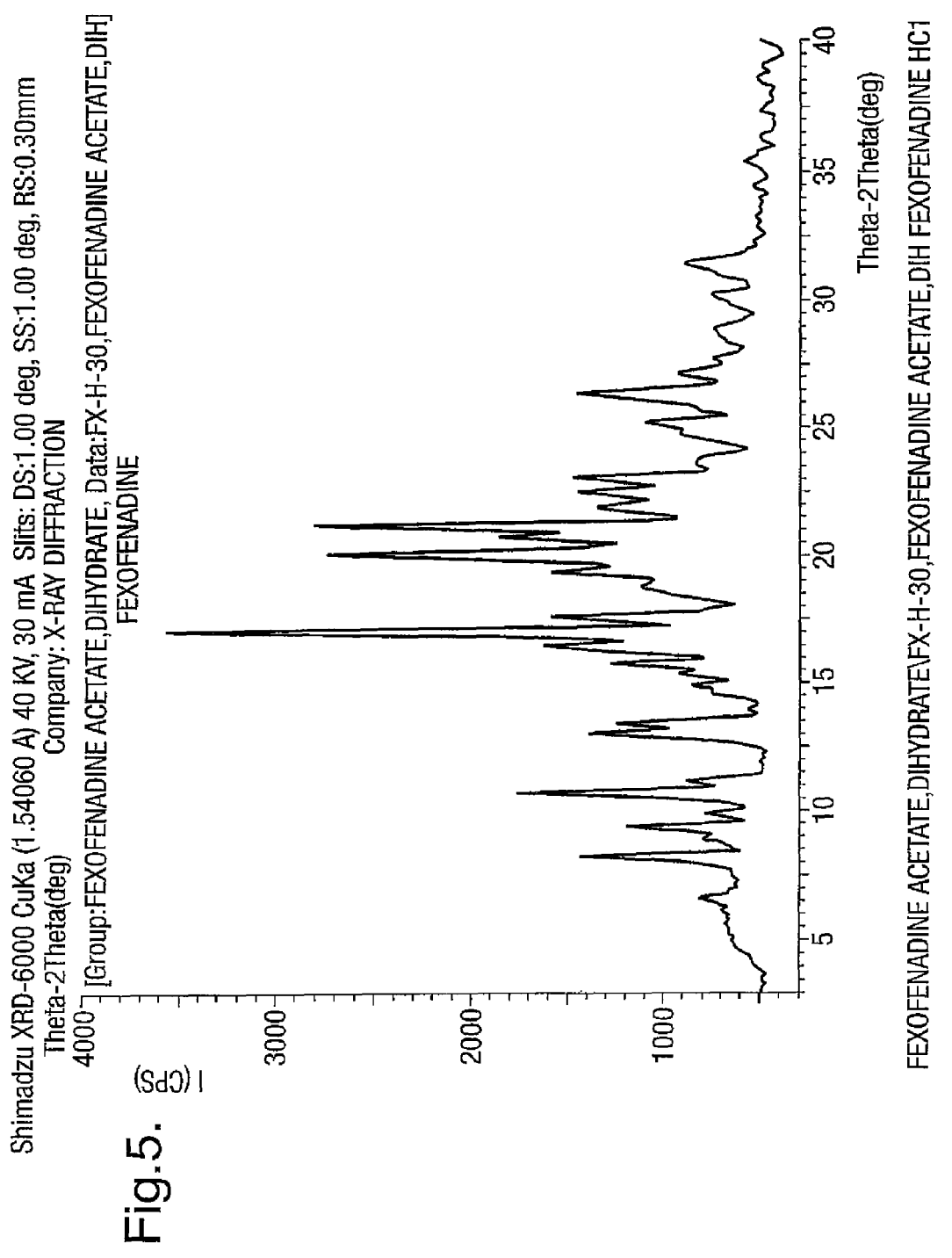
FIG. 5 is a PXRD pattern of fexofenadine acetate dihydrate.
Figure 6:
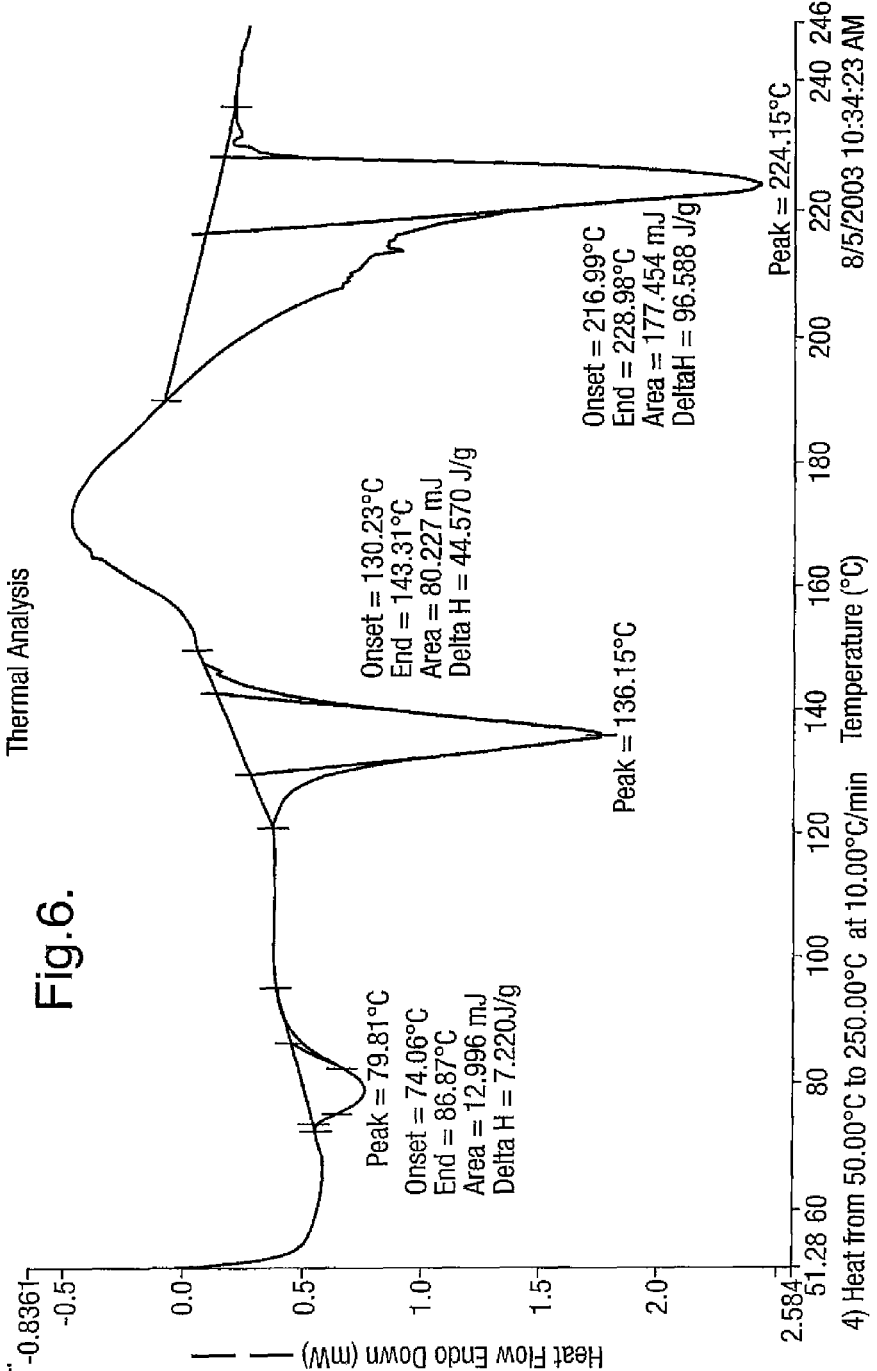
FIG. 6 is a DSC pattern of fexofenadine acetate dihydrate.

16. A process comprising contacting the crystalline fexofenadine free base monohydrate Form F according to claim 2 with acetic acid to form the pharmaceutically acceptable salt of anhydrous crystalline fexofenadine acetate monohydrate Form E characterised as having an X-ray diffraction pattern, or substantially the same X-ray diffraction pattern, as shown in FIG. 5.

* * * * *